US00PP33288P2

(12) United States Plant Patent
Wood

(10) Patent No.: US PP33,288 P2
(45) Date of Patent: Jul. 27, 2021

(54) ***DIERVILLA* PLANT NAMED 'SMDCS'**

(50) Latin Name: *Diervilla rivularis*
Varietal Denomination: SMDCS

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/115,063

(22) Filed: Dec. 8, 2020

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Diervilla* plant named 'SMDCS' is disclosed, characterized by a dense plant habit and attractive foliage throughout Spring, Summer and Fall. The new variety is a *Diervilla*, normally produced as an outdoor garden or container plant.

2 Drawing Sheets

Latin name of the genus and species: *Diervilla rivularis*. Variety denomination: 'SMDCS'.

BACKGROUND OF THE INVENTION

The new *Diervilla* cultivar is a product of a planned breeding program conducted by the inventor in Grand Haven, Mich. The objective of the breeding program was to produce ornamental plants with new colors and habits. The open pollination resulting in this new variety was made during August of 2011.

The new *Diervilla* 'SMDCS' resulted from an open pollination in which seed was collected from the seed parent, *Diervilla rivularis* 'SMNDRSF', U.S. Plant Pat. No. 27,550. Accurate identification of the pollen parent impossible. The new variety was identified as a potentially interesting selection during the Summer of 2014, at a research nursery in Grand Haven, Mich.

Asexual reproduction of the new cultivar 'SMDCS' by softwood cuttings was first performed during the Summer of 2014 at research greenhouse in Grand Haven, Mich. Subsequent asexual propagation has shown that the unique features of this cultivar are stable and reproduced true to type in at least 4 successive generations.

SUMMARY OF THE INVENTION

The cultivar 'SMDCS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMDCS'

These characteristics in combination distinguish 'SMDCS' as a new and distinct *Diervilla* cultivar:

1. Attractive foliage through Spring, Summer and Fall.
2. Dense plant habit.

PARENT COMPARISON

Plants of the new cultivar 'SMDCS' are similar to plants of the seed parent, in most horticultural characteristics, however, plants of the new cultivar 'SMDCS' differ in the following:

1. Spring foliage of the new variety is green; Spring foliage of the parent is black.
2. The new variety has dark burgundy Fall foliage color, the seed parent has burgundy to black Fall foliage.

COMMERCIAL COMPARISON

Plants of the new cultivar 'SMDCS' can also be compared to the known variety *Diervilla* 'G2X885411' U.S. Plant Pat. No. 28,403. The varieties are similar in most horticultural characteristics, however 'SMDCS' differs in the following:

1. The new variety has darker green Summer foliage than this comparator.
2. Fall color of the new variety is dark burgundy; Fall color of this comparator is reddish-green.
3. Foliage of the new variety is wider than foliage of this comparator.

BRIEF DESCRIPTION OF THE PHOTOGRAPHS

Figure 1:
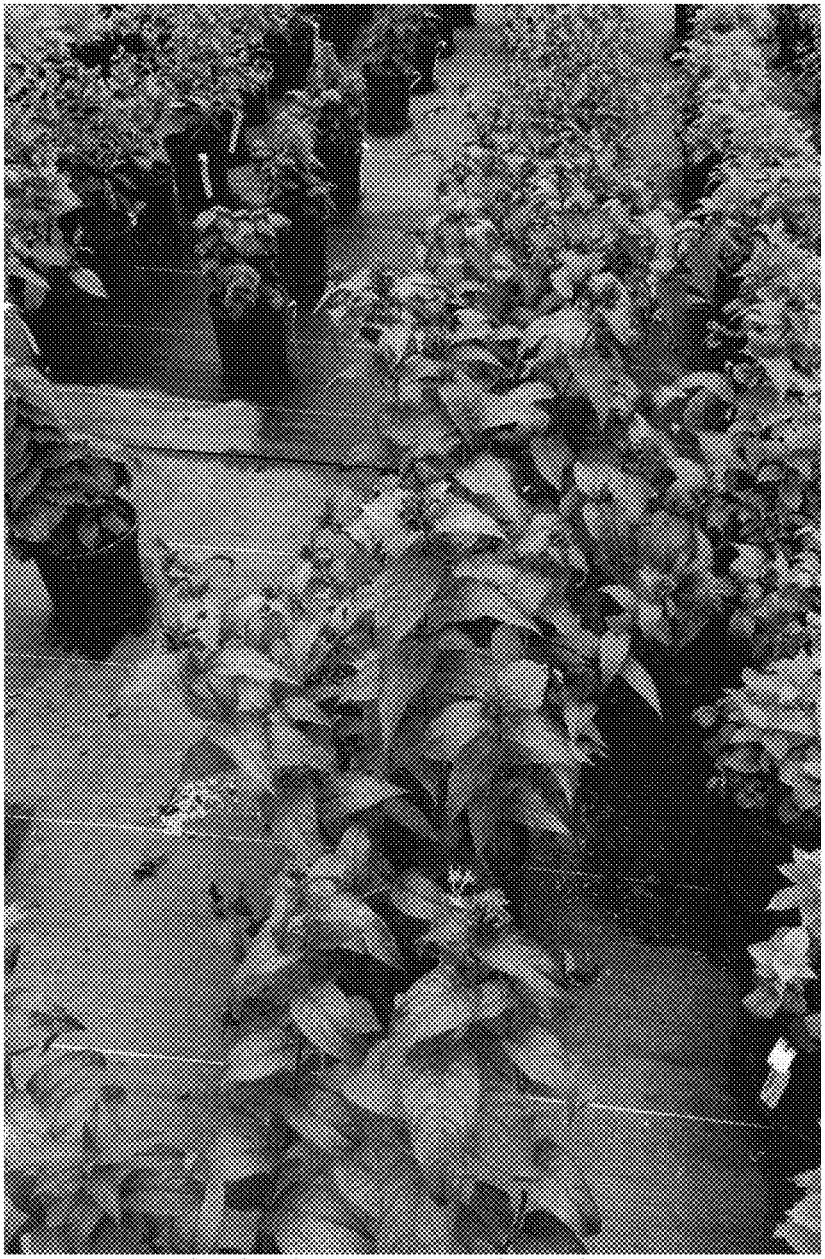

The accompanying photograph in FIG. 1 illustrates in full color typical plants of 'SMDCS', with burgundy Fall foliage grown in 2 gallon containers. Plants are about 2 years old.

Figure 2:
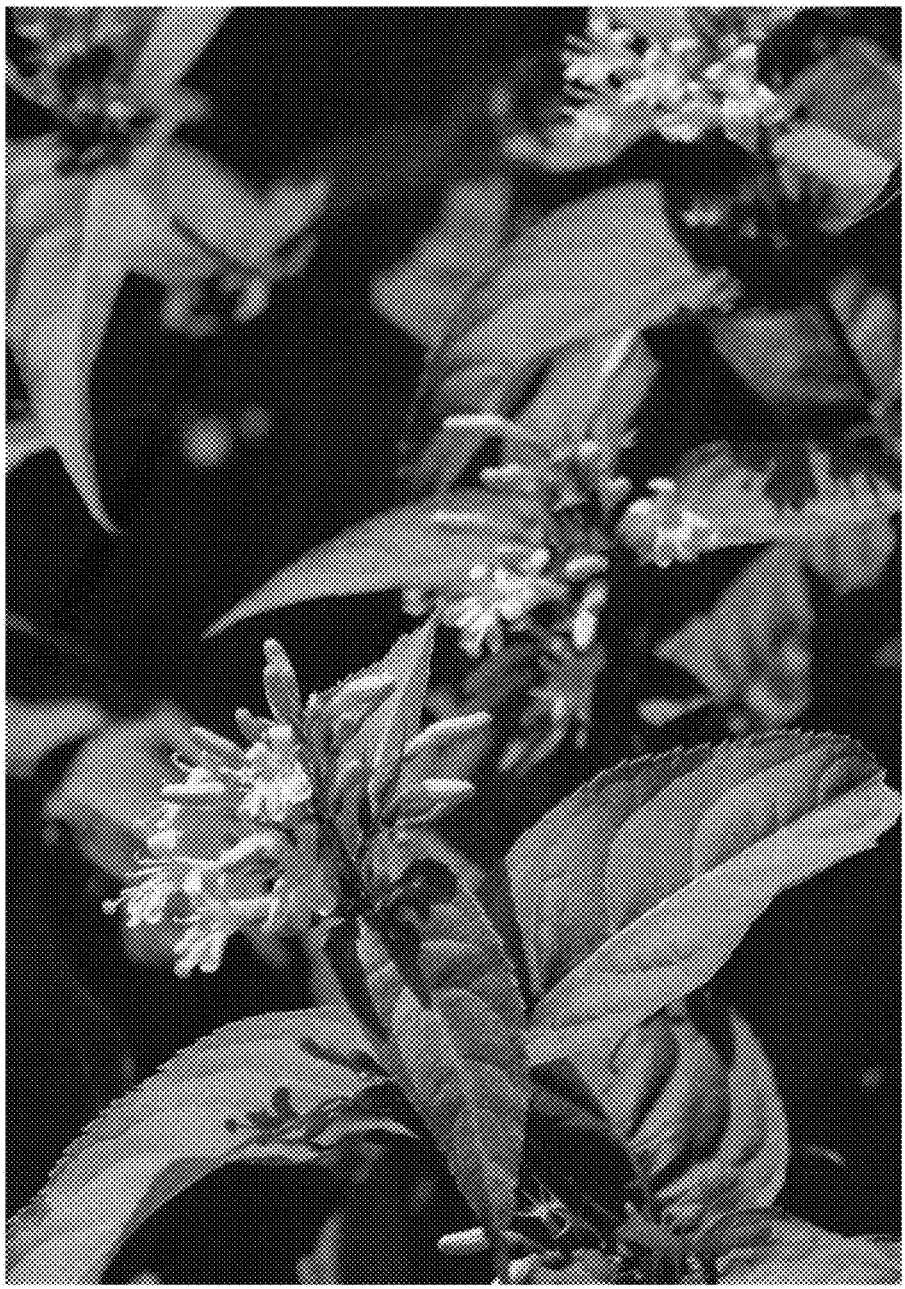

FIG. 2 illustrates in full color a typical inflorescence and green Summer foliage of 'SMDCS' grown outdoors in Grand Haven, Mich., in a garden setting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMDCS' plants grown in a poly house in Grand Haven, Mich. Measurements were taken during August of 2020. The plants were approximately 2 years old. The growing temperature ranged from 18° C. to 27° C. during the day, and 5° to 10° C. at night. Measurements and numerical values represent averages of typical plant types. Botanical classification: *Diervilla rivularis* 'SMDCS'.

PROPAGATION

Time to initiate roots: About 10 to 21 days at approximately 18 to 27° C.
Root description: Between fleshy and fibrous, moderately dense and moderately freely branching. Roots white to tan, not accurately measured with R.H.S. chart.
Time to produce a liner: About 28 days.

PLANT

Plant type: Perennial shrub.
Age of plant described: Approximately 2 years old.
Pot size of plant described: 1 gallon pot, previously pruned.
Growth habit: Upward and outwards.
Overall plant shape: Rounded, upright.
Height: Approximately 36 cm.
Plant spread: Approximately 25 cm.
Growth rate: Moderate to rapid.
Plant vigor: Vigorous.
Branching characteristics: Basal, pinching required.
Length of primary lateral branches: Approximately 30 cm.
Diameter of lateral branches: Approximately 4 mm.
Quantity of lateral branches: 6 main basal branches.
Stem:
- *Shape*.—Rounded.
- *Strength*.—Moderate.
- *Stem pubescence*.—Yes.
- *Stem color*.—Near RHS Greyed-Orange 176B.

Internode length: Average range 5 to 7 cm.

FOLIAGE

Leaf:
- *Arrangement*.—Opposite.
- *Average length*.—Approximately 7.5 to 10.5 cm.
- *Average width*.—Approximately 3.75 to 5.75 cm.
- *Shape of blade*.—Lanceolate.
- *Apex*.—Acuminate.
- *Base*.—Obtuse.
- *Margin*.—Serrate.
- *Texture of top surface*.—Leathery.
- *Texture of bottom surface*.—Leathery with distinct veins.
- *Color*.—Young foliage upper side: Near RHS Green NN137A. Young foliage under side: Near RHS Yellow-Green 147B. Mature foliage upper side: Near RHS Greyed-Green N189A. Mature foliage under side: Near RHS Green NN137D. Fall color upper side: Near RHS Greyed-Purple 183B. Fall color upper side: Near RHS Greyed-Purple 183B.
- *Venation*.—Type: Pinnate Venation color upper side: Near RHS Yellow-Green 144C, flushed Greyed-Red 182C late Summer. Venation color under side: Near RHS Green 139D.
- *Petiole*.—Average Length: Approximately 8 mm. Diameter: Approximately 5 mm. Petiole color upper side: Near RHS Yellow-green 144C with slight overlay of Greyed-Red 182C. Petiole color lower side: Near RHS Yellow-Green 144C with slight overlay of Greyed-Red 182C. Petiole Texture: Pubescent.

FLOWER

Natural flowering season: Late Summer.
Inflorescence type and habit: Terminal cyme.
Quantity of flowers per inflorescence: About 30.
Inflorescence size:
- *Diameter*.—About 5.5 cm.
- *Height*.—About 3.9 cm.

Individual flowers:
- *Flower form*.—Salverform.
- *Flower aspect*.—Upright and outward.
- *Size*.—Flower Diameter: Approximately 1.5 cm. Flower Length: Approximately 2 cm. Flower throat Diameter: Approximately 3 mm. Flower tube Diameter: Approximately 2 mm. Flower tube length: Approximately 9 mm.
- *Persistence*.—Self-cleaning.
- *Fragrance*.—None.

Petal:
- *Petal arrangement*.—Single whorl.
- *Number of petals per flower*.—5.
- *Petal appearance*.—Smooth to velvet-like (slightly pubescent).
- *Petal shape*.—Oblong.
- *Tip shape*.—Obtuse.
- *Margin*.—Undulate.
- *Length*.—7 mm from throat.
- *Width*.—2 mm.
- *Texture*.—Upper: Smooth, velvety pubescence. Lower: Smooth, velvety pubescence. Tube texture: Slight, soft pubescence. Throat texture: Smooth.

Petal color:
- *When opening*.—Upper surface: Near RHS Yellow-Green N144B. Lower surface: Near RHS Yellow-Green N144B.
- *Fully opened*.—Upper surface: Near RHS Yellow-Green N144B. Lower surface: Near RHS Yellow-Green N144B. Flower tube color: Near RHS Yellow-Green N144B. Flower throat color: Near RHS Yellow-Green N144B with a stripe of Yellow 5A.

Petaloids: None present.
Bud:
- *Shape*.—Oblong.
- *Length*.—1.3 cm.
- *Diameter*.—3 mm.
- *Color*.—Near RHS Yellow-Green 150B.

Sepals:
- *Shape*.—Narrow deltate.
- *Arrangement*.—Whorl.
- *Length*.—Approximately 3 mm.

*Width*.—Approximately 0.5-1 mm.
*Margin*.—Entire.
*Base*.—Tapered.
*Tip*.—Acuminate.
*Number*.—5.
*Color*.—Near RHS Yellow-Green N144C.

Peduncle:
*Length*.—6 mm.
*Diameter*.—1 mm.
*Color*.—Near RHS Green 143B.
*Orientation*.—0-45°.
*Strength*.—Strong.
*Texture*.—Smooth.

Pedicel:
*Length*.—4 mm.
*Diameter*.—1 mm.
*Angle*.—0-25°.
*Strength*.—Moderate.
*Texture*.—Smooth to slightly pubescent.
*Color*.—Near RHS Green 143B flushed Greyed-Red 183C.

REPRODUCTIVE ORGANS

Stamens:
*Number*.—5.
*Filament length*.—Approximately 5 mm.
*Filament color*.—Near RHS Yellow-green 145D.

Anthers:
*Shape*.—Linear.
*Length*.—3 mm.
*Color*.—Near RHS Orange 24D.
*Pollen*.—Scant.
*Pollen color*.—Near RHS Orange 24D.

Pistil:
*Number*.—1.
*Length*.—1.4 cm.
*Style*.—Length: 1.5 cm. Color: Near RHS yellow-green 144B.
*Stigma*.—Shape: Round. Color: Near RHS Yellow-green 144B. Ovary color: Near RHS Yellow-Green 144B.

OTHER CHARACTERISTICS

Garden performance: Very good performance in the garden, resistant to typical environmental stresses such as wind, sun and extreme temperatures.

Disease/pest resistance: Good resistance to Disease and Pests.

Temperature tolerance: The new variety tolerates temperatures between −29 to 35° C.

What is claimed is:

1. A new and distinct cultivar of *Diervilla* plant named 'SMDCS' as herein illustrated and described.

* * * * *